United States Patent
Blier et al.

(10) Patent No.: US 8,025,642 B2
(45) Date of Patent: Sep. 27, 2011

(54) POWERED VARIABLE SEAL DIAMETER TROCAR EMPLOYING A LONGITUDINAL DISPLACEMENT MECHANISM

(75) Inventors: Kenneth Blier, Cheshire, CT (US); Michael Bettuchi, Middletown, CT (US)

(73) Assignee: Tyco Health Group LP, New Haven, CT (US)

( * ) Notice: Subject to any disclaimer, the term of this patent is extended or adjusted under 35 U.S.C. 154(b) by 0 days.

(21) Appl. No.: 12/715,682

(22) Filed: Mar. 2, 2010

(65) Prior Publication Data

US 2010/0249710 A1  Sep. 30, 2010

Related U.S. Application Data

(60) Provisional application No. 61/163,557, filed on Mar. 26, 2009.

(51) Int. Cl.
*A61M 5/178* (2006.01)
(52) U.S. Cl. .............. 604/167.06; 604/167.01
(58) Field of Classification Search ............ 604/167.01, 604/167.06, 167.03, 164.01, 164.02, 165.01
See application file for complete search history.

(56) References Cited

U.S. PATENT DOCUMENTS

| | | | |
|---|---|---|---|
| 4,177,814 A * | 12/1979 | Knepshield et al. ............ 604/26 |
| 4,723,550 A | 2/1988 | Bales et al. | |
| 5,334,164 A | 8/1994 | Guy et al. | |
| 5,350,364 A | 9/1994 | Stephens et al. | |
| 5,549,651 A | 8/1996 | Lynn | |
| 5,913,847 A | 6/1999 | Yoon | |
| 6,245,045 B1 * | 6/2001 | Stratienko ............... 604/164.13 |
| 2005/0092944 A1 | 5/2005 | Patterson | |
| 2008/0294125 A1 | 11/2008 | Focht et al. | |

FOREIGN PATENT DOCUMENTS

| | | |
|---|---|---|
| EP | 0426407 | 5/1991 |
| EP | 0510851 | 10/1992 |

OTHER PUBLICATIONS

European Search Report, Application No. EP 10250572.4 dated Jun. 10, 2010.

* cited by examiner

*Primary Examiner* — Nicholas D Lucchesi
*Assistant Examiner* — Jenna Zhang

(57) ABSTRACT

An apparatus for sealing a passageway through an access assembly includes a variable seal member having an orifice for reception of an instrument therethrough. Each of a pair of compression members has a pressure face for contacting the variable seal member, each pressure face opposing the variable seal member from an opposite longitudinal side, and each compression member moveable with respect to the other compression member in a longitudinal direction transverse to the pressure faces. The compression members may be moved in the longitudinal direction to adjust the degree of compressive force exerted on the portal seal member and thus adjust a diameter of the orifice to effectively interface with the instrument to form a fluid tight relation therewith.

14 Claims, 3 Drawing Sheets

POWERED VARIABLE SEAL DIAMETER TROCAR EMPLOYING A LONGITUDINAL DISPLACEMENT MECHANISM

CROSS REFERENCE TO RELATED APPLICATION

The present application claims the benefit of and priority to U.S. Provisional Application Ser. No. 61/163,557 filed on Mar. 26, 2009, the entire contents of which are incorporated herein by reference.

BACKGROUND

1. Technical Field

The present disclosure relates generally to a surgical portal apparatus employing a system for maintaining a fluid-tight seal across a passageway for surgical instruments. In particular, the disclosure relates to a portal apparatus employing a variable diameter seal with a longitudinal displacement mechanism in communication with a power source for accommodating instruments of various sizes.

2. Background of Related Art

Surgical procedures such as laparoscopic, arthroscopic, and endoscopic procedures in general are termed minimally invasive at least in part because the incision required is relatively small, perhaps one inch in length or less. Small incisions are preferred because they are inherently less traumatic to the surrounding body tissue. Also, small incisions subject internal organs to a limited exposure to the contaminants in the outside atmosphere. Thus, small incisions enable shorter hospital stays and faster recoveries with less pain and scarring than is common with the larger incisions required for conventional surgery.

Endoscopic surgery is possible due in part to the availability of instruments designed specifically for this purpose. A trocar assembly, for example, may include a sharp trocar or obturator for creating a small incision, and a cannula assembly for providing a conduit through the incision once the obturator has been removed. A cannula is an elongated tube, typically 5 mm to 13 mm in diameter, which may be configured to have a distal end inserted into an internal body cavity adjacent an operative site. The body cavity is often inflated with an insufflation gas, carbon dioxide for example, to separate the body wall from vital organs. This provides a space where a surgeon may introduce viewing equipment or maneuver tools into position without damaging surrounding tissue. Various other instruments may then be inserted and withdrawn through the cannula for access to the working space and operative site. In order to fit through a cannula and enable a surgeon to manipulate tissue far removed from the incision, instruments adapted for endoscopic surgery typically include a long and narrow cylindrical shaft. The exact size and shape of the instrument shaft, however, may vary for the many instruments required for a single procedure.

Endoscopic procedures generally require that any instrumentation inserted into the patient's body be sealed, i.e. provisions must be made to ensure insufflation gasses, blood and other fluids do not escape the body through the cannula. Furthermore, a seal acts to prevent contamination of the body cavity by the outside environment. In the absence of such a fluid-tight seal, many of the attendant advantages of minimally invasive surgery are lost.

A dual seal system is commonly employed wherein a first seal is normally biased to a closed condition to seal the conduit in the absence of an instrument, and a second seal configured to form a fluid-tight interface with the shaft of an instrument. The second seal must be adaptable to accommodate the various instrument sizes and geometries. Often the second seal takes the form of a septum seal, which is a generally flat, elastomeric member having an orifice therethrough. The orifice may be sized such that the smallest instrument may not pass through the septum seal without engaging and forming a seal with the elastic material. The elasticity of the septum seal permits the orifice to expand to accommodate the largest instrument.

An aspect of concern in the use of such a septum seal is the contact pressure applied by the septum seal on the instrument shaft. If the contact pressure is insufficient, the insufflation pressure may not be maintained as the surgeon manipulates the instrument. If the contact pressure is too great, however, the surgeon may experience difficulty in advancing and properly controlling the instrument. Because larger instruments must expand the orifice to a greater degree, the contact pressure is consequently larger than for smaller instruments, and thus larger instruments may be more difficult to manipulate than smaller instruments. Accordingly, a need exists for an apparatus for forming a seal about an instrument inserted through a cannula that is capable of accommodating variously sized instruments while ensure a proper contact pressure.

SUMMARY

The present disclosure describes a surgical portal apparatus which permits a surgical instrument to access a tissue site while maintaining a seal about the instrument. The portal apparatus includes a portal member, which is dimensioned for positioning within body tissue and defines a longitudinal axis. A longitudinal passageway through the portal member provides access to the tissue site. A variable seal member is mounted to the portal member and includes an orifice having a diameter dependent upon a longitudinal dimension of the variable seal member. Each of a pair of compression members is disposed on an opposite longitudinal side of the variable seal member, and each compression member has a pressure face for contacting variable seal member. A longitudinal displacement mechanism in communication with a power source is adapted to produce relative longitudinal motion between the compression members such that the longitudinal dimension of the variable seal is altered to vary the diameter of the orifice.

The diameter of the orifice may be dependent upon a Poission's ratio of a material of the variable seal member. The material may be elastomeric or the material may comprise a viscoelastic gel. The variable seal member may include a flexible casing containing a predetermined quantity of a fluid, and the casing may define a toroidal geometry. An electromagnet may be provided as a component of the longitudinal displacement mechanism. A control feature in communication with the longitudinal displacement mechanism may be included for adjusting the longitudinal dimension of the variable seal to a predetermined value. The control feature may include circuitry responsive to a diameter of an instrument inserted into the longitudinal passageway. A triggering mechanism may be adapted to detect an introduction of an instrument into the longitudinal passageway.

In another aspect of the disclosure, a surgical portal apparatus permits a surgical instrument to access a tissue site while maintaining a seal about the instrument. The portal apparatus includes a portal member, which is dimensioned for positioning within body tissue and defines a longitudinal axis. A longitudinal passageway through the portal member provides access to the tissue site. A septum seal member is mounted to the portal member and includes an orifice having a diameter dependent upon a longitudinal dimension of the septum seal member. Each of a pair of compression members is disposed on an opposite longitudinal side of the septum seal member, and each compression member has a pressure face for contacting septum seal member. A longitudinal displacement mechanism is adapted to produce relative longitudinal motion between the compression members such that the longitudinal dimension of the septum seal is altered to vary the diameter of the orifice.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Figure 1:
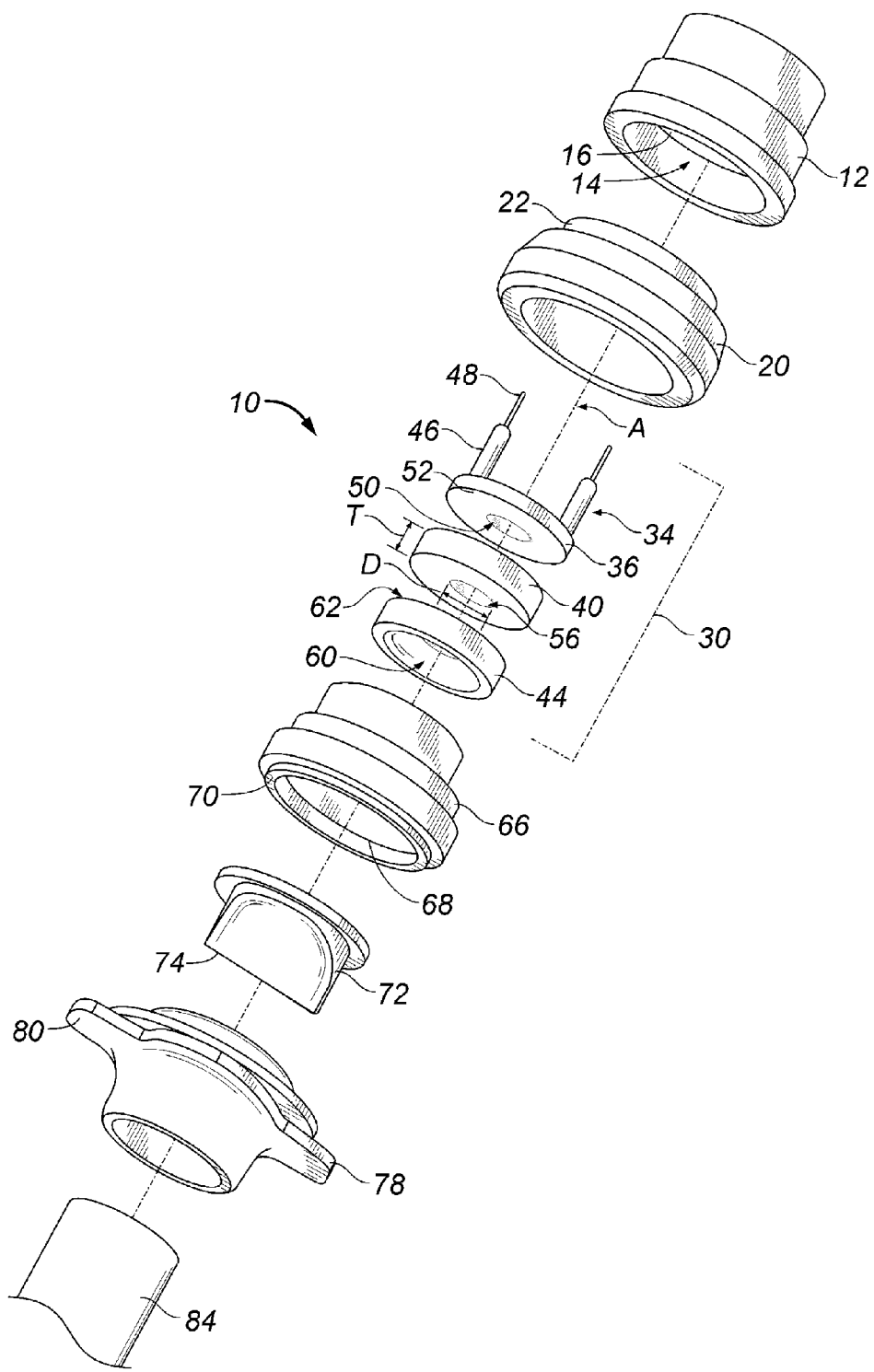
FIG. 1 is an exploded perspective view of a surgical portal apparatus in accordance with the present disclosure.

The present disclosure contemplates the introduction into a person's body of all types of surgical instruments including clip appliers, graspers, dissectors, retractors, staplers, laser fibers, photographic devices, endoscopes and laparoscopes, tubes, and the like. All such objects are referred to herein generally as "instruments." In the drawings and in the description which follows, the term "proximal," as is traditional, will refer to the direction toward the operator or a relative position on the surgical device or instrument which is closer to the operator, while the term "distal" will refer to the direction away from the operator or relative position of the instrument which is further from the operator.

Referring initially to FIG. 1, a surgical portal apparatus according to the present disclosure is depicted generally as 10. At the proximal end, a cap 12 is open to provide an entryway for an instrument into the portal apparatus 10. The interior of cap 12 includes a central opening 14 and a radial overhang 16. Central opening 14 extends through cap 12 and defines a central longitudinal axis "A," which extends centrally through the surgical portal apparatus 10. Radial overhang 16 defines a transition in the diameter of central opening 14, such that central opening 14 is wider distally of radial overhang 16 than proximally of radial overhang 16. Radial overhang 16 may define a plane orthogonal to axis "A." Proximal housing 20 is also hollow and open at both ends. An annular ridge 22 provides for a fluid-tight interface with cap 12 and may abut radial overhang 16.

A variable diameter seal 30 is housed within proximal housing 20, and generally includes a longitudinal displacement mechanism 34, a proximal compression member 36, a compressible septum seal 40, and a distal compression member 44. Longitudinal displacement mechanism 34 is configured to selectively vary the longitudinal distance between proximal and distal compression members 36, 44. Here, a pair of pneumatic cylinders 46 having extendible pistons 48 are coupled to proximal compression member 36. Proximal compression member 36 is a generally rigid component having an instrument passage 50 and a distal pressure face 52, which is adapted for contact with septum seal 40.

Septum seal 40 is a generally planar, washer shaped component having an orifice 56 for engaging an instrument in a fluid-tight, but low-pressure manner. In an uncompressed state as shown, septum seal 40 has a thickness "T" and an inner orifice diameter "D." When compressed, as discussed below with reference to FIG. 2B, septum seal 40 assumes a reduced thickness "t," and, as a consequence, also assumes a reduced orifice diameter "d." This reduction in orifice diameter permits a fluid tight-interface between septum seal 40 and an instrument inserted through orifice 56. The materials comprising septum seal 40 may include an elastomeric material such as polyisoprene. Alternatively, septum seal 40 may include a material exhibiting some flow characteristics such as a viscoelastic gel or foam material.

Distal compression member 44 is a generally rigid component having an instrument passage 60 and a proximal pressure face 62. The proximal pressure face 62 of distal compression member 44 opposes the distal pressure face 52 of proximal compression member 36. Distal compression member 44 and proximal compression member 36 are movable in a longitudinal direction relative to one another such that their respective pressure faces 62, 52 may be approximated to compress septum seal 40 and separated to relax septum seal 40.

Seal support 66 is rigidly coupled to proximal housing 20 and provides an interior shelf 68 upon which distal compression member 44 may rest. In some cases, such as the configuration depicted in FIG. 1, distal compression member 44 may be incorporated into seal support 66 such that interior shelf 68 serves the function of pressure face 52. Because it is not required to translate in this embodiment, distal compression member 44 need not be a discrete and distinct component.

A circumferential ridge 70 on a distal surface seal support 66 provides a seat for duckbill valve 72. Duckbill valve 72 is an elastomeric member with a pair of distally extending substantially flat lips 74 which are normally biased together to create a substantial fluid-tight seal through the portal apparatus in the absence of an instrument. Lips 74 may be easily separated upon the insertion of an instrument from the proximal side. The use of other zero-closure valves is also contemplated.

Distal housing 78 encloses duckbill valve 72 and forms a fluid-tight connection with proximal housing 20. On the exterior, distal housing 78 includes diametrically opposed extensions 80 which provide a surface for a surgeon or operator to grip the portal apparatus 10 with two fingers. Distal housing 78 receives cannula 84 and forms a fluid-tight interface therewith. Cannula 84 is a hollow tube open at both ends providing a passageway for an instrument through a small incision made in a patient. A distal end (not shown) of cannula 84 may be positioned in a body cavity adjacent a tissue site, while the proximal end coupled to distal housing 78 remains external to the patient.

Figure 2A:
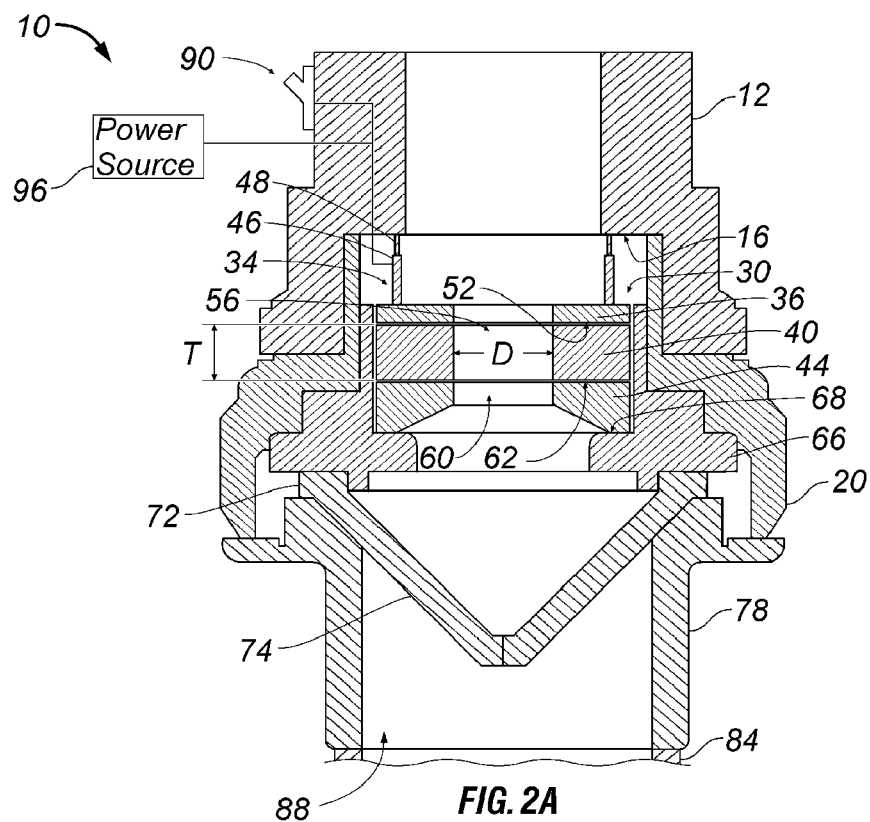
FIG. 2A is a cross sectional view of the portal apparatus of FIG. 1 illustrating a variable diameter seal in an initial condition for receiving an instrument.

Referring now to FIG. 2A, a longitudinal passageway 88 extends through surgical portal apparatus 10. Only the lips 74 of duckbill valve 72 interrupt passageway 88, which is otherwise clear to accommodate an instrument. Variable diameter seal 30 is disposed between radial overhang 16 of cap 12 and interior shelf 68 of seal support 66. Because of the rigid interfaces that connect the cap 12 and seal support 66, radial overhang 16 remains at a fixed distance from interior shelf 68.

A user interface 90 is depicted schematically on an exterior surface of cap 12 in operative communication with longitudinal displacement mechanism 34. User interface 90 may include a toggle switch as shown permitting a surgeon or operator to selectively approximate or separate compression members 36, 44. Alternatively, user interface 90 may include a plurality of control surfaces allowing an operator to select appropriate values for variables such as an instrument diameter or desired seal pressure. Also, user interface 90 may be positioned as depicted, or at any other convenient location.

Also depicted schematically is power source 96 in communication with longitudinal displacement mechanism 34. Power source 96 may comprise a supply of compressed air, electrical power or another source of energy for activating longitudinal displacement mechanism 34.

Figure 2B:
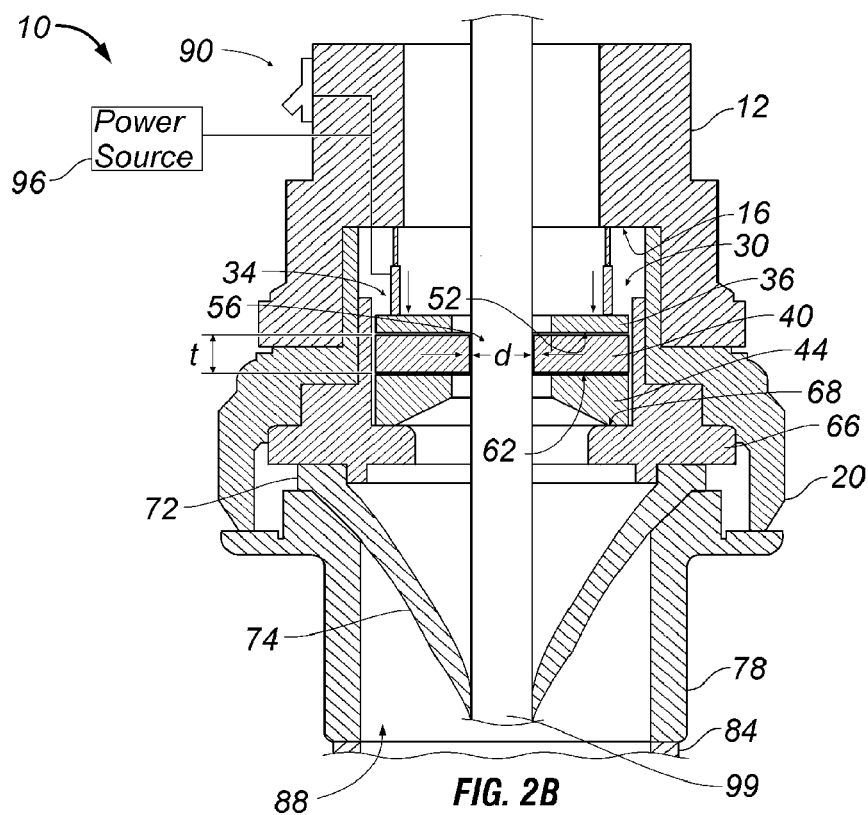
FIG. 2B is a cross sectional view of the portal apparatus illustrating the variable diameter seal in an activated condition for sealing an instrument.

The use of surgical portal apparatus 10 is now described with reference to FIGS. 2A and 2B. The surgeon may first introduce a shaft 99 of a surgical instrument through cap 12 in a distal direction. The shaft 99 may include the shaft of an obturator of a trocar assembly (not shown) or any general instrument. A surgeon may position a distal end of cannula 84 adjacent a surgical site and establish an insufflation pressure. Duckbill valve 72 prevents insufflation gasses from escaping through the passageway 88 in the absence of an instrument. Shaft 99 may pass freely through orifice 56 of septum seal 40 when it is in an uncompressed condition as in FIG. 2A. If the surgeon further advances the shaft 99 through the lips 74 of duckbill seal 72, the seal across passageway 88 will be compromised. The surgeon may therefore wish to establish a seal about shaft 99 with variable diameter seal 30.

The surgeon may manipulate user interface 90 to activate longitudinal displacement mechanism 34. This results in pistons 48 extending from cylinders 46 and forcing proximal compression member 36 in a distal direction. Pressure faces 52, 62 are approximated and septum seal 40 is compressed to a reduced thickness "t" as depicted in FIG. 2B. The reduction in thickness is indicative of a longitudinal strain in septum seal 40. For a strained body to remain in equilibrium, the longitudinal strain must be accompanied by an opposite lateral strain in an orthogonal direction. This means that as the thickness "T" of septum seal 40 is reduced to thickness "t," there is a tendency for a width of septum seal 40 to increase. Because the outer circumference of septum seal 40 is constrained by seal support 66, this tendency manifests itself in a convergence or flow of the material of septum seal 40 adjacent orifice 56 radially inwardly about shaft 99, thus forming a seal therewith.

With a seal about shaft 99 in place, the surgeon may manipulate tissue at the surgical site. The surgeon will likely make adjustments to the position and orientation of the instrument while in use and the variable diameter seal 30 may be adapted to provide the surgeon with this required flexibility. When the surgeon is finished with the instrument, the instrument shaft 99 may be withdrawn first through duckbill valve 72. The lips 74 will return to their biased closed position reestablishing the seal across the passageway 88.

The surgeon may then manipulate user interface 90 to cause longitudinal displacement mechanism 34 to separate the pressure faces 52, 62. When the pressure causing the longitudinal strain is relieved, septum seal returns to its original uncompressed condition having thickness "T" and orifice diameter "D." The portal apparatus 10 is then ready for the process to be repeated with an additional instrument.

The use described above presents at least one opportunity to control the contact pressure associated with septum seal 40. The contact pressure may be controlled by controlling the size of orifice diameter "d" simply by controlling the pressure generated by longitudinal displacement mechanism 34. For a septum seal 40 formed from a material associate with a given Poisson's ratio, i.e. the material property defined by the negative ratio of transverse strain to longitudinal strain, orifice diameter "d" decreases with a decreasing strained thickness "t." Therefore, longitudinal displacement mechanism 34 may be configured to provide a greater pressure for smaller instruments than for larger instruments to provide an appropriate orifice diameter "d" for each instrument.

Figure 3A:
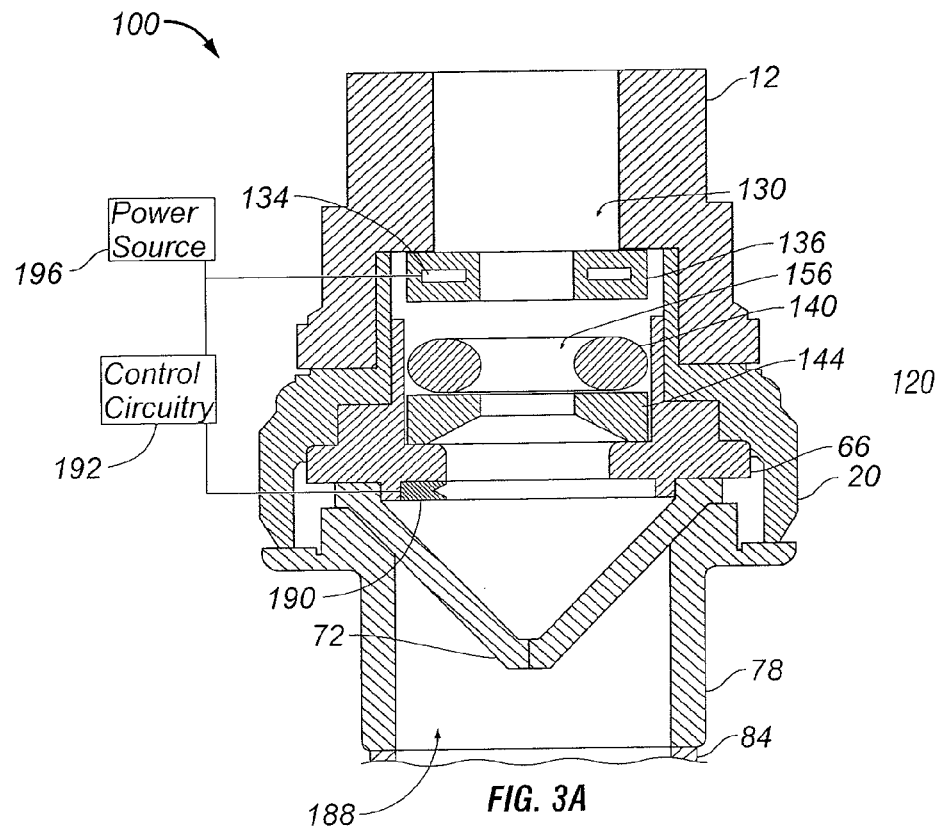
FIG. 3A is a cross sectional view of an alternate embodiment of the surgical portal apparatus illustrating a variable diameter seal in an initial condition.
Figure 3B:
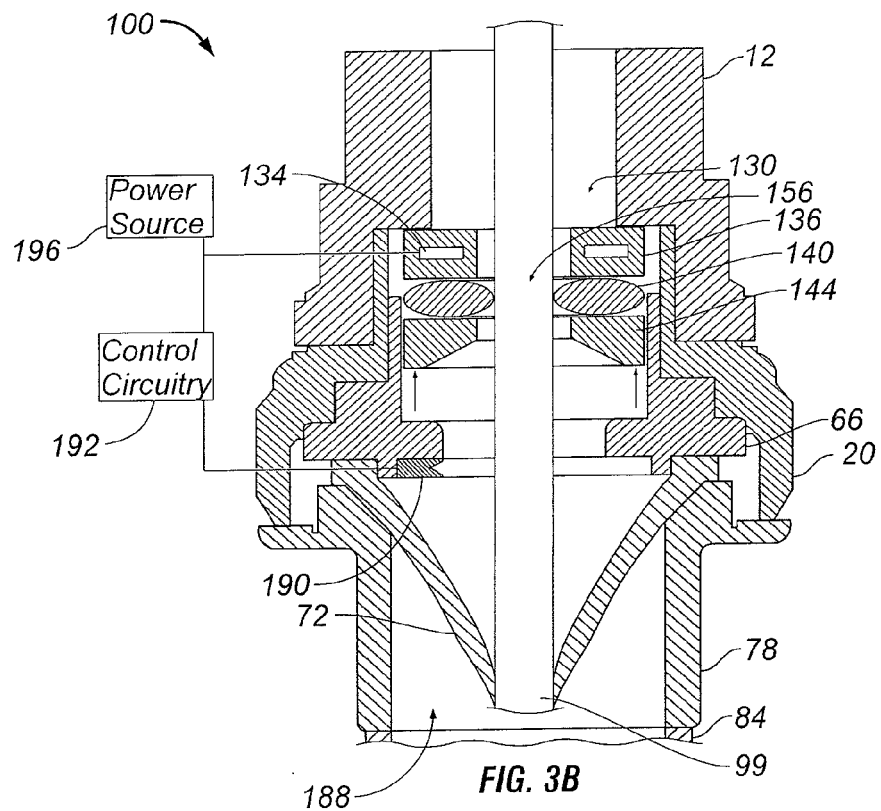
FIG. 3B is a cross sectional view of the surgical portal apparatus of FIG. 3A illustrating the variable diameter seal in an activated condition.

Referring now to FIGS. 3A and 3B, another embodiment of a surgical portal apparatus in accordance with the disclosure is depicted generally as 100. Cap 12, proximal housing 20, seal support 66, duckbill valve 72, distal housing 78 and cannula 84 may all operate identically as described above to provide a sealed passageway to a surgical site. Surgical portal apparatus 100 employs an alternate variable diameter seal 130 may to provide a seal about an instrument.

Variable diameter seal 130 includes a longitudinal displacement mechanism comprising an electromagnet 134 contained within proximal compression member 136. Proximal compression member 136 may be rigidly coupled to cap 12 so that it is stationary with respect to portal assembly 100. Because it may be stationary in this embodiment, it is not necessary that proximal compression member 136 be a distinct and discrete component. For example, electromagnet 134 may be incorporated into cap 12 such that cap 12 may serve the function of proximal compression member 136.

Seal 140 comprises a flexible casing that may contain a predetermined amount of fluid. The shape of seal 140 may be toroidal such that seal 140 may assume at least a normal unstressed geometry as depicted in FIG. 3A, or a flattened geometry as depicted in FIG. 3B. Distal compression member 144 is disposed distally of seal 140 and comprises a magnetic or ferromagnetic material allowing it to be selectively attracted by the electromagnet 134. An orifice 156 through seal 140 may thus be selectively altered to create a seal about an instrument shaft 99.

Also included in portal apparatus 100 is longitudinal passageway 188, a triggering mechanism such as sensor 190 and control circuitry 192. Sensor 190 and control circuitry 192 are in operative communication with one another, and also with electromagnet 134. Sensor 190 is adapted to detect the presence of an instrument within passageway 188. Several arrangements are contemplated wherein sensor 190 may also detect the diameter of the instrument present within passageway 188.

A cooperative arrangement is contemplated for sensor 190 where the instrument shaft 99 is specially configured to communicate diameter information. For example, the instrument shaft 99 may contain a passive radio-frequency identification (RFID) tag that responds to queries transmitted by sensor 190 when the RFID tag is in close proximity to the sensor 190. The RFID tag may respond with an appropriate signal identifying the instrument by diameter. Alternatively, a cooperative arrangement may include a barcode or other size identification markings on the instrument shaft 99 that may be read by an optical sensor 190.

A passive arrangement is also contemplated where the sensor 190 is able to determine the instrument diameter from the physical characteristics of the instrument shaft 99. For example, a transmitter (not shown), such as an ultrasound transducer or light emitting element, may transmit signals that can be reflected by the instrument shaft 99 upon its entry into passageway 188. Sensor 190 may be configured to detect the intensity and location of the reflections to determine the instrument diameter.

In either a passive or cooperative arrangement, sensor 190 may provide a signal to control circuitry 192 indicating the presence and possibly the size of shaft 99. Control circuitry 192 is adapted to control the magnitude of the current supplied to electromagnet 134 based on the signal. The magnetic flux density generated by electromagnet 134 is based on the magnitude of the supplied current and dictates the attractive force applied to distal compression member 144. A power source 196 is included to provide energy to the electromagnet 134 and sensor 190.

In use, a surgeon may insert instrument shaft 99 into the passageway 188 of surgical portal apparatus 100. The shaft may pass freely through seal 140 in a normal unstressed state as shown in FIG. 3A. When the shaft 99 is detected by sensor 190, a signal may be directed to control circuitry 192 indicating the presence and possibly the size of shaft 99. Control circuitry 190 may process this information and activate electromagnet 134 to the degree necessary to produce a fluid-tight seal about shaft 99 with an appropriate contact pressure. When electromagnet 134 is activated, distal compression member 144 is drawn toward proximal compression member 136 thereby flattening seal 140 and reducing the diameter of orifice 156. The degree to which orifice 156 is reduced is dependent upon the attractive force generated between proximal and distal compression members 136, 144. Control circuitry 192 may therefore be adapted to supply electromagnet 194 with a greater magnitude of current when a smaller instrument is detected than when a larger instrument is detected. This may produce an appropriate contact pressure for any size shaft 99.

Although the foregoing disclosure has been described in some detail by way of illustration and example, for purposes of clarity or understanding, it will be obvious that certain changes and modifications may be practiced within the scope of the appended claims.

What is claimed is:

1. A surgical portal apparatus for permitting access to a tissue site, which comprises:
   a portal member dimensioned for positioning within body tissue and defining a longitudinal axis, the portal member having a longitudinal passageway therethrough providing access to a tissue site;
   a variable seal member mounted to the portal member, the variable seal member having an orifice therethrough, the orifice having a diameter dependent upon a longitudinal dimension of the variable seal member;
   a pair of compression members longitudinally disposed on opposite sides of the variable seal member, each compression member having a pressure face for contacting the variable seal member; and
   a longitudinal displacement mechanism in communication with a power source coupled to the surgical portal apparatus, the longitudinal displacement mechanism adapted to receive energy from the power source to automatically produce relative longitudinal movement between the compression members such that the longitudinal dimension of the variable seal member is altered to vary the diameter of the orifice.

2. The surgical portal apparatus according to claim 1, wherein the variable seal member comprises a material associated with a Poisson ratio, the diameter of the orifice dependent upon the Poisson ratio.

3. The surgical portal apparatus according to claim 2, wherein the material associated with a Poisson ratio is elastomeric.

4. The surgical portal apparatus according to claim 2, wherein the material associated with a Poisson ratio is a viscoelastic gel.

5. The surgical portal apparatus according to claim 1, wherein the variable diameter seal member comprises a casing containing a predetermined quantity of a fluid.

6. The surgical portal apparatus according to claim 5, wherein the variable diameter seal member defines a toroidal geometry.

7. The surgical portal apparatus according to claim 1, wherein the longitudinal displacement mechanism comprises an electromagnet.

8. The surgical portal apparatus according to claim 1, wherein the surgical portal apparatus further comprises a control feature in communication with the longitudinal displacement mechanism, the control feature adapted to cause the longitudinal displacement mechanism to adjust the longitudinal dimension of the variable seal member to a predetermined value.

9. The surgical portal apparatus according to claim 8, wherein the control feature comprises circuitry responsive to a diameter of an instrument inserted into the longitudinal passageway.

10. The surgical portal apparatus according to claim 1, wherein the surgical portal apparatus further comprises a triggering mechanism in communication with the longitudinal displacement mechanism, the triggering mechanism adapted to detect an introduction of an instrument into the longitudinal passageway.

11. The surgical portal apparatus according to claim 1, wherein the power source comprises at least one of the group consisting of a supply of compressed air and a supply of electrical energy.

12. The surgical portal apparatus according to claim 11, wherein the longitudinal displacement mechanism comprises at least one longitudinally extendable piston operatively coupled to the power source.

13. The surgical portal apparatus according to claim 1, wherein the power source and the longitudinal displacement mechanism are operatively coupled to a toggle switch, and wherein the toggle switch is movable from a first position in which the longitudinal displacement mechanism permits the compression members to remain in a longitudinally separated relation and a second position wherein the longitudinal displacement mechanism induces the compression members to move to a relatively longitudinally approximated relation.

14. A surgical portal apparatus for permitting access to a tissue site, which comprises:
   a portal member dimensioned for positioning within body tissue and defining a longitudinal axis, the portal member having a longitudinal passageway therethrough providing access to a tissue site;
   a septum seal member mounted to the portal member, the septum seal member having an orifice therethrough, the orifice having a diameter dependent upon a longitudinal dimension of the septum seal member;
   a pair of compression members longitudinally disposed on opposite sides of the septum seal member, each compression member having a pressure face for contacting the septum seal member;
   a longitudinal displacement mechanism, the longitudinal displacement mechanism adapted to produce relative motion between the compression members such that the longitudinal dimension of the septum seal member is altered to vary the diameter of the orifice; and
a toggle switch operatively coupled to the longitudinal displacement mechanism such that the toggle switch is movable from a first position in which the longitudinal displacement mechanism permits the compression members to remain in a longitudinally separated relation and a second position in which the longitudinal displacement mechanism induces the compression members to move to a relatively longitudinally approximated relation.

* * * * *

UNITED STATES PATENT AND TRADEMARK OFFICE
CERTIFICATE OF CORRECTION

| | | |
|---|---|---|
| PATENT NO. | : 8,025,642 B2 | Page 1 of 1 |
| APPLICATION NO. | : 12/715682 | |
| DATED | : September 27, 2011 | |
| INVENTOR(S) | : Kenneth Blier et al. | |

It is certified that error appears in the above-identified patent and that said Letters Patent is hereby corrected as shown below:

Title Page item 73

The first page of U.S. Patent 8,025,642B2 incorrectly shows the Assignee's name as: Tyco Health Group LP The correct Assignee name is: Tyco Healthcare Group LP Signed and Sealed this
Eighth Day of November, 2011

David J. Kappos
*Director of the United States Patent and Trademark Office*